United States Patent [19]
Kleshinski et al.

[11] Patent Number: 5,540,712
[45] Date of Patent: *Jul. 30, 1996

[54] STENT AND METHOD AND APPARATUS FOR FORMING AND DELIVERING THE SAME

[75] Inventors: Stephen J. Kleshinski, Scituate; Morris A. Simon, Boston; Dmitry Rabkin, Brookline, all of Mass.

[73] Assignee: Nitinol Medical Technologies, Inc., Boston, Mass.

[ * ] Notice: The term of this patent shall not extend beyond the expiration date of Pat. No. 5,354,308.

[21] Appl. No.: 252,198

[22] Filed: Jun. 1, 1994

Related U.S. Application Data

[63] Continuation-in-part of Ser. No. 167,661, Dec. 16, 1993, Pat. No. 5,395,390, which is a continuation of Ser. No. 878,184, May 1, 1992, Pat. No. 5,354,308.

[51] Int. Cl.$^6$ ............................ A61M 29/00; A61F 2/06
[52] U.S. Cl. ............................................ 606/198; 623/1
[58] Field of Search .................................. 606/191, 192, 606/195, 198; 604/96, 104–106, 284; 623/1, 12

[56] References Cited

U.S. PATENT DOCUMENTS

| | | |
|---|---|---|
| 3,868,956 | 3/1975 | Alfidi et al. . |
| 4,170,990 | 10/1979 | Baumgart et al. . |
| 4,503,569 | 3/1985 | Dotter . |
| 4,512,338 | 4/1985 | Balko et al. . |
| 4,553,545 | 11/1985 | Maass et al. . |
| 4,655,771 | 4/1987 | Wallsten . |
| 4,733,665 | 3/1988 | Palmaz . |
| 4,739,762 | 4/1988 | Palmaz . |
| 4,830,003 | 5/1989 | Wolff et al. . |
| 5,064,435 | 11/1991 | Porter . |
| 5,078,720 | 1/1992 | Burton et al. . |
| 5,135,536 | 8/1992 | Hillstead . |
| 5,139,480 | 8/1992 | Hickle et al. . |
| 5,178,618 | 1/1993 | Kandarpa ........................ 606/198 |
| 5,192,307 | 3/1993 | Wall .............................. 606/198 |
| 5,354,308 | 10/1994 | Simon ............................ 623/1 |
| 5,354,309 | 10/1994 | Schnepp-Pesch .................. 606/198 |
| 5,395,390 | 3/1995 | Simon ............................ 606/198 |
| 5,404,200 | 4/1994 | Spaulding . |
| 5,405,377 | 4/1995 | Cragg ........................... 606/198 |

FOREIGN PATENT DOCUMENTS

| | | |
|---|---|---|
| 0518838 | 6/1992 | European Pat. Off. . |
| 0556850 | 8/1993 | European Pat. Off. . |
| 0565251 | 10/1993 | European Pat. Off. . |

*Primary Examiner*—Michael A. Brown
*Attorney, Agent, or Firm*—Sixbey, Friedman, Leedom & Ferguson

[57] ABSTRACT

A stent including a wire skeletal frame, the frame being adapted to assume a first condition in which the frame is relatively rigid and substantially tubular in configuration and a second condition in which the frame is flexible, of reduced stress, and collapsible, such that in the second condition walls of the frame are adapted to be positioned against each other to form a stent diameter substantially equal to the combined thickness of the frame walls in abutting engagement with each other, the frame in its second condition being substantially devoid of bias therein urging the frame to assume the first configuration.

32 Claims, 7 Drawing Sheets

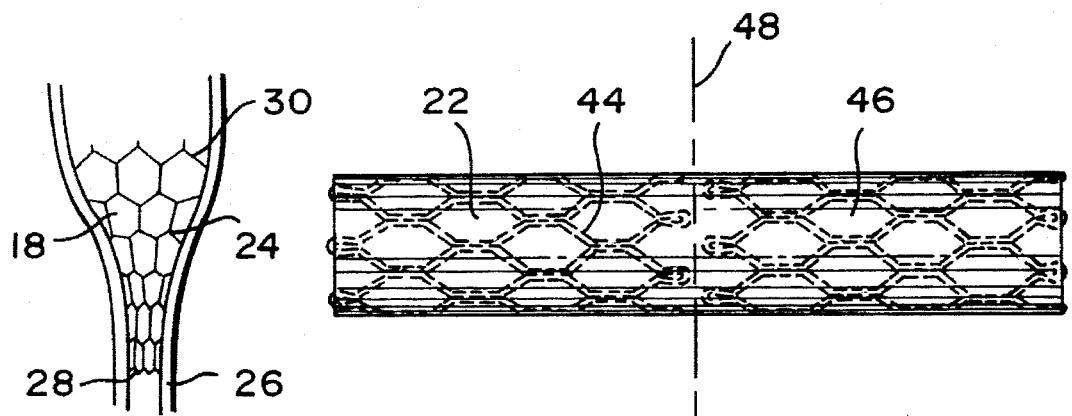
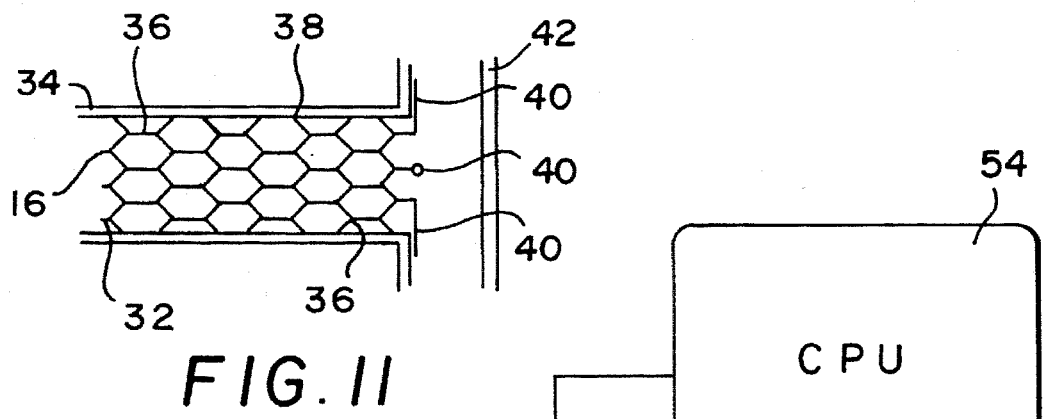
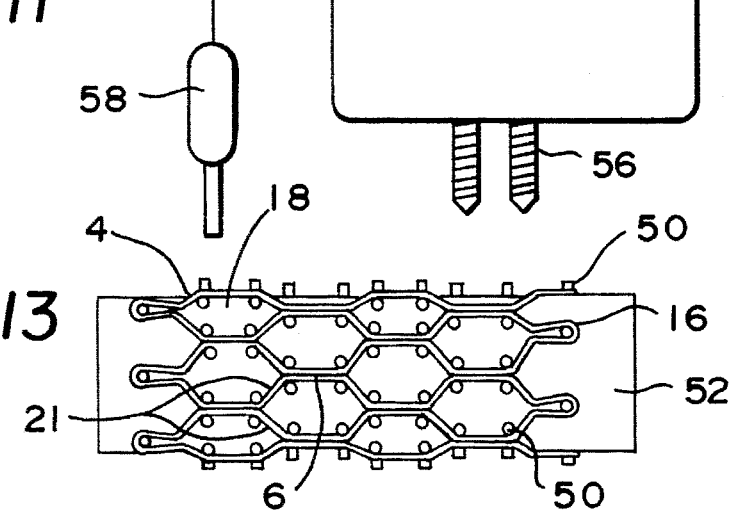

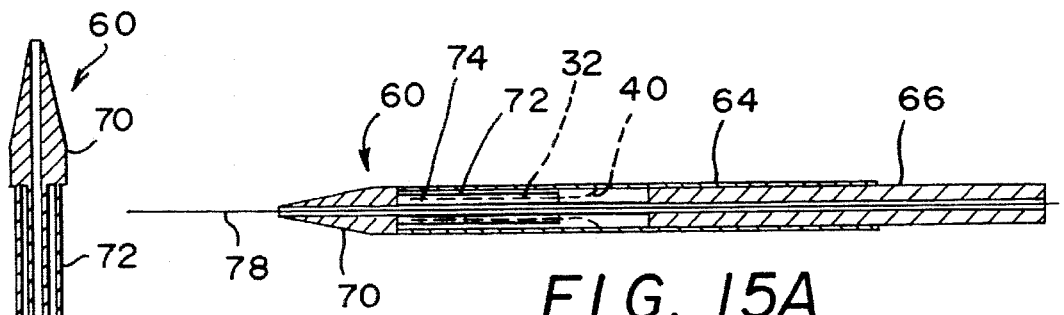
FIG. 15A
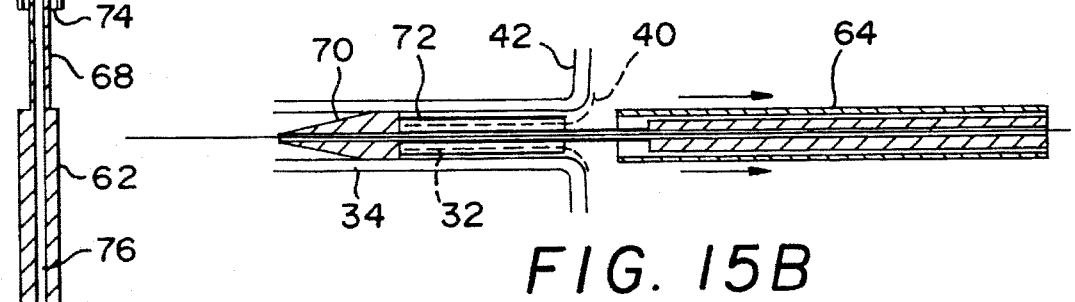
FIG. 15B
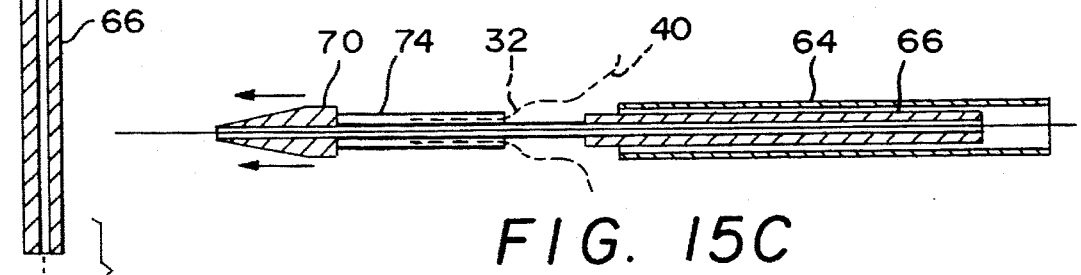
FIG. 15C
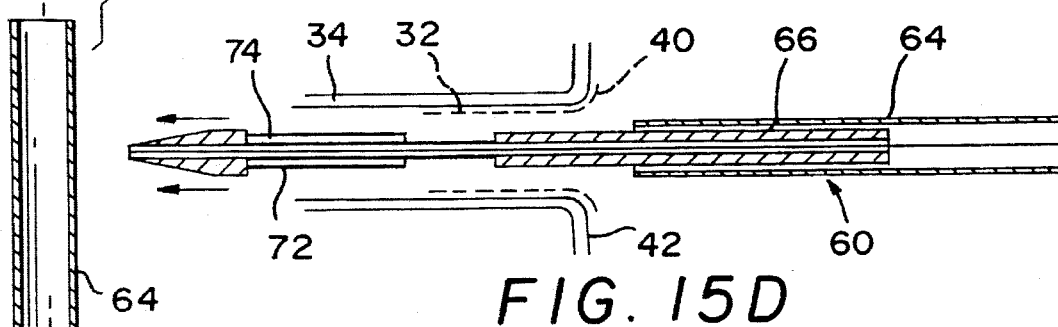
FIG. 15D
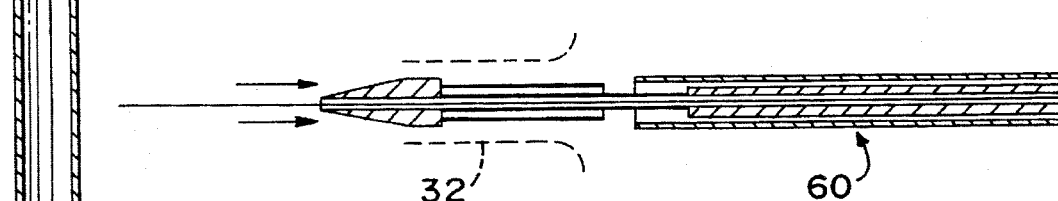
FIG. 15E
FIG. 14

STENT AND METHOD AND APPARATUS FOR FORMING AND DELIVERING THE SAME

This application is a continuation-in-part application of application Ser. No. 08/167,661 filed Dec. 16, 1993, now U.S. Pat. No. 5,395,390 which is a continuation of Ser. No. 07/878,184 filed May 1, 1992, now U.S. Pat. No. 5,354,308.

BACKGROUND OF THE INVENTION

1. Field of the Invention

This invention relates to stents and is directed more particularly to a self-expanding stent which is repositionable after being set in place.

2. Brief Description of the Prior Art

Self-expanding stents are generally known in the art. U.S. Pat. No. 4,580,568, issued Apr. 8, 1986, to Cesare Gianturco, discloses an endovascular stent formed of stainless steel wire. The stent is compressed into a reduced size having an outer diameter substantially smaller than the stent in its expanded shape. The stent is held in its compressed state during its passage through a small bore catheter until delivered into a vascular system passageway, whereupon the stress in the stent causes the stent to expand in the larger bore vascular passageway to hold open the passageway. When the stent is compressed, the bends in the wire, which is of a zig-zag configuration, store stress, and the stent is expandable by the release of the stress stored in the bends. Once set in place, the radial extremities of the stent bear against the inside walls of the passageway. There is no ready means by which the stent may be again compressed, or softened, so that the stent may be repositioned.

It would be beneficial to the medical arts to have available a stent adapted for compression into a small size to facilitate introduction into a vascular passageway, and adapted for self-expansion in the vascular passageway to hold open the passageway, and also adapted to be softened and/or contracted to permit repositioning of the stent.

SUMMARY OF THE INVENTION

It is, therefore, an object of the invention to provide a stent adapted to assume a first configuration in which the stent is expanded, capable of exercising considerable stress if confined, as by a vessel wall, and substantially tubular in configuration for holding open a vascular passageway, and a second configuration in which the stent is flexible, in a reduced stress state, and adapted to be compressed into a small enough size to fit within the small bore of a delivery catheter.

A further object of the invention is to provide such a stent which is adapted to change from the first condition of relative rigidity to the second condition of flexibility and reduced stress, by exposure to a preselected transition temperature, such that the stent may be relaxed in place in a vascular passageway by cooling to facilitate repositioning thereof without damage to walls of the passageway.

A still further object of the invention is to provide such a stent laminated within an elastomeric sleeve, the sleeve being expandable to conform to the stent's first, i.e. rigid, condition and having therein a bias towards assuming a smaller size, such that upon the stent's assuming the second, i.e. flexible, condition, the sleeve operates to compress the stent to a size less than its expanded size.

Yet another object of the present invention is to provide such a stent formed from a plurality of cells each having first and second spaced, substantially parallel cell sides which are joined to one of the first or second cell sides of an adjacent cell. The cell sides of all of the cells are substantially parallel to the central longitudinal axis of the stent or the stent section which the cells form.

A further object of the present invention is to provide such a stent formed from a plurality of cells, each of which includes first and second spaced, straight side portions which are joined to one of the first or second straight side portions of an adjacent cell. The straight side portions of all cells are substantially parallel to the central longitudinal axis of the stent or the stent section which the cells form. The ends of each cell are closed by end portions which extend between the adjacent ends of each side portion at an angle to the central longitudinal axis of the stent or the stent section which the cells form. These end portions are not connected to adjacent cells.

A further object of the present invention is to provide such a stent formed from stent sections having different structural configurations and/or which provide different amounts of outward radial force when the stent sections are expanded from a collapsed disposition.

A further object of this invention is to provide a stent delivery unit which facilitates anchoring of the proximal end of the stent in place before expansion of the distal end.

A still further object of the present invention is to provide a novel and improved method and apparatus for forming a stent of thermal memory material wherein the cells forming the stent are welded before the stent is heat treated to thermally determine the shape memory for the stent.

With the above and other objects in view, as will hereinafter appear, a feature of the present invention is the provision of a stent comprising a wire skeletal frame, the frame being adapted to assume a first condition in which the frame is expanded and resiliently deformable but relatively rigid, the frame being further adapted to assume a second condition in which the frame is flexible, of reduced stress and collapsible, such that in the second condition walls of the frame are adapted to be positioned in their collapsed disposition, and further adapted to be positioned against each other to form a stent diameter substantially equal to the combined thickness of the frame walls in abutting engagement with each other, and further adapted to be positioned between the expanded disposition and the walls abutting engagement disposition, the frame in the second condition being substantially devoid of bias present therein urging the frame to assume the first configuration.

In accordance with a further feature of the invention, there is provided a stent, as described immediately above, and further comprising an elastomeric sleeve disposed on the stent and expandable therewith to conform to the stent's expanded condition, the sleeve having therein a bias exerting a compressive force on the stent, such that upon cooling of the stent below a selected transition temperature, the sleeve urges the flexible and low stress stent to a third configuration smaller than the stent in its expanded condition and larger than the stent in its walls abutting configuration.

The above and other features of the invention, including various novel details of construction and combinations of parts, will now be more particularly described with reference to the accompanying drawings and pointed out in the claims. It will be understood that the particular devices embodying the invention are shown by way of illustration only and not as limitations of the invention. The principles and features of this invention may be employed in various and numerous embodiments without departing from the scope of the invention.

BRIEF DESCRIPTION OF THE DRAWINGS

Reference is made to the accompanying drawings in which are shown illustrative embodiments of the invention, from which its novel features and advantages will be apparent.

In the drawings:

FIG. 10 is a side elevational view of a third embodiment of the stent of the present invention;

FIG. 11 is a side elevational view of a fourth embodiment of the stent of the present invention;

FIG. 12 is a side elevational view of a fifth embodiment of the stent of the present invention;

FIG. 13 is a block diagram showing the mechanism used to manufacture the stent of the present invention;

FIG. 14 is a sectional exploded view of a stent delivery unit of the present invention; and FIG. 15A–15E are sectional views illustrating the manner in which the stent delivery unit of FIG. 14 positions a stent.

DESCRIPTION OF THE PREFERRED EMBODIMENT

Figure 1:
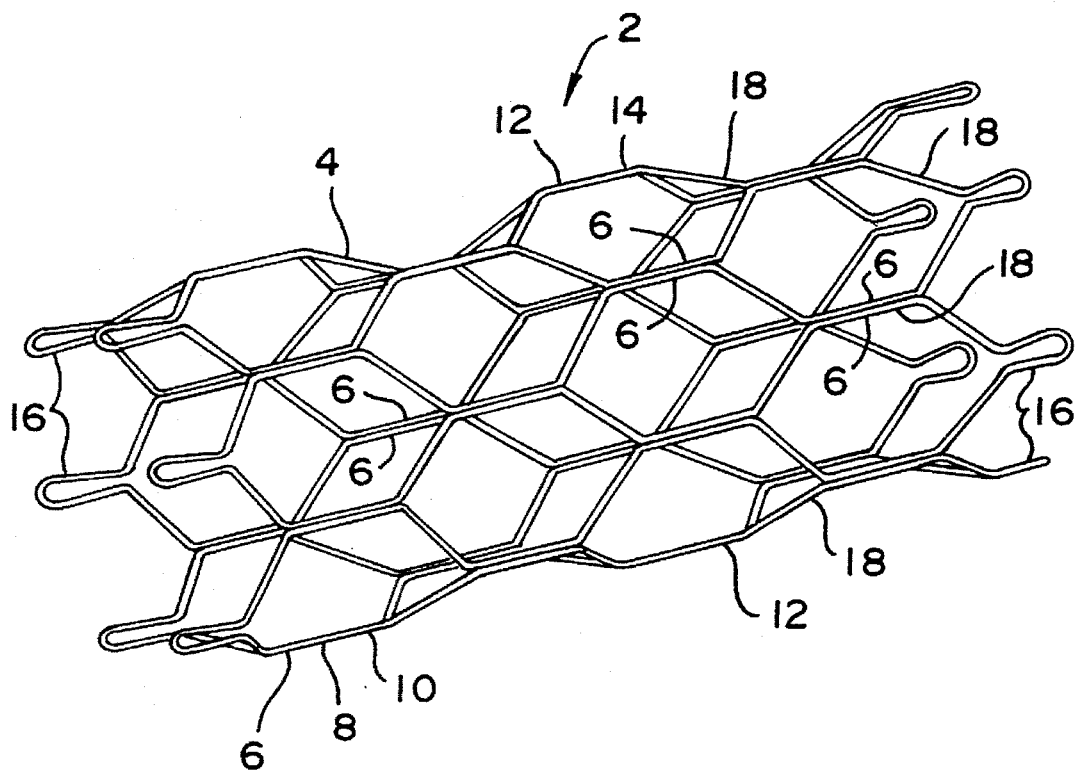
FIG. 1 is a perspective view of one form of stent illustrative of an embodiment of the invention.
Figure 2:
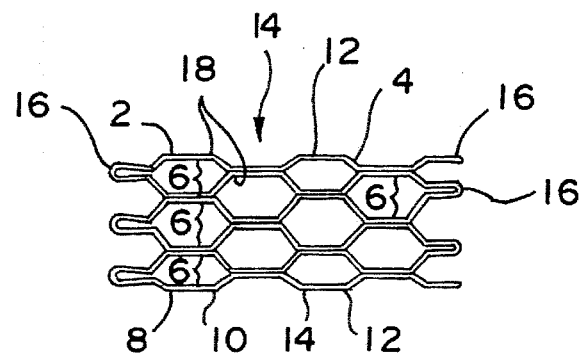
FIG. 2 is a side elevational view thereof.

Referring to FIGS. 1 and 2, it will be seen that an illustrative stent includes a skeletal frame 2, preferably formed from a single wire 4. The wire 4 includes a plurality of abutting straight portions 6 which are joined to each other, as by welding.

In FIGS. 1 and 2, the illustrative stent is shown in a first condition in which the frame 2 is expanded, relatively rigid, and substantially tubular in configuration. Ends 8, 10 of the single wire 4 are disposed in one of the welded straight portions 6, such that there are no exposed wire free ends, disposed within or extending from the frame 2. The abutting and elongated straight portions 6 of the wire 4 facilitate the use of strong elongated welds to securely join the wire portions 6 together. The wire 4 preferably is round in cross-section, but may be formed of any desired cross-sectional shape. In the frame straight portions 6 the joined wire segments are disposed, relative to the tubular configuration of the frame, circumferentially thereof. The wire 4 abuts itself only at the straight portions 6 and does not cross itself at any point. Accordingly, the frame walls, that is, walls 12 of a tubular body portion 14 of the frame 2 have a thickness equal to the diameter of the wire 4.

Figure 3:
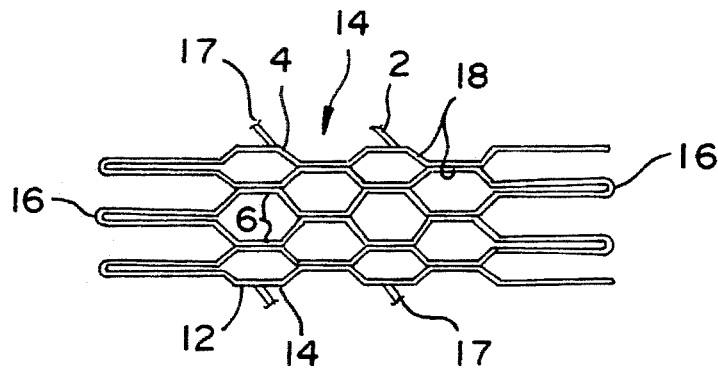
FIG. 3 is a side elevational view of an alternative embodiment thereof.

The stent includes the body portion 14 and finger portions 16 extending generally axially from one, or both, ends of the body portion. The fingers facilitate a gradual reduction in radially outwardly extending pressure exerted by the stent on the wall of a vascular passageway in which the stent is located. Such gradual reduction of pressure facilities acceptance of the stent by the passageway and reduces deleterious reactions by the passageway wall to the presence of the stent. Referring to FIG. 3, it will be seen that the finger portion 16 may be extended further axially to lessen the probability of adverse reaction by the passageway wall to the pressure exerted against the wall by the stent frame 2. Also, hooks or barbs 17 can be attached to project outwardly from some of the straight portions 6 to aid in anchoring the stent to the vessel in which it is implanted. These hooks can be formed from Nitinol in either its memory form or superelastic form, or they can be formed from other material such as biologically resorbable polymers.

Figure 4:
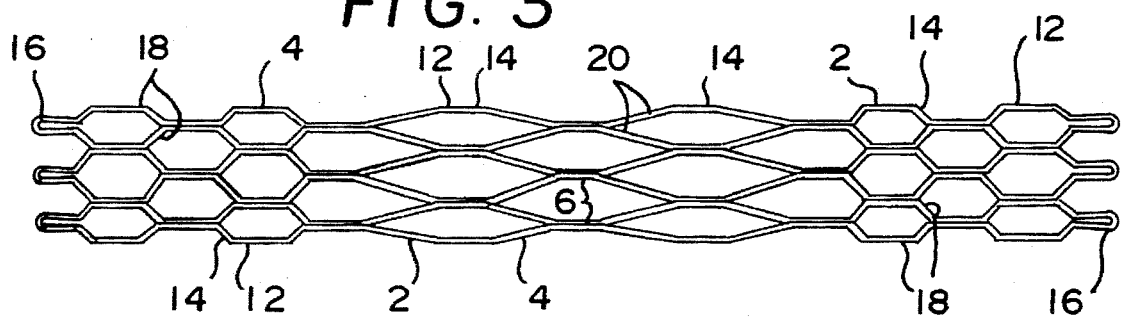
FIG. 4 is a side elevational view of a second alternative embodiment thereof.

The tubular body portion 14 comprises a mesh formed by the wire 4, the mesh comprising a plurality of interconnected cells 18 which are preferably of a polygonal configuration when viewed in plan, providing spaced, substantially parallel straight sides to form the aforementioned straight portions 6. The cells 18, when polygonal, are preferably of a hexagonal configuration, which readily provides expansion and rigidity characteristics desirable in the structure and operation of the device. Preferably, the stent comprises six of the polygonal cells 18 circumferentially and an even number of the polygonal cells along its length, thereby facilitating formation of the stent by the single wire 4. The portion of the stent having the mesh construction exercises a substantially greater radial bias than do the finger portions 16. Thus, when it is desired to have more force near the ends of the stent than at its center, the embodiment shown in FIG. 4 may be used. Referring to FIG. 4, it will be seen that in this embodiment, the central portion of the tubular body portion 14 includes elongated cells 20 exercising less radial force than the cells 18.

It is important to note that each cell is formed by two straight portions 6 which are substantially parallel to the central longitudinal axis of the stent or stent section of which the cell is a part. Each end of the cell is closed by an end wall or end walls 21 which extend between adjacent ends of the straight portions 6; the end walls being disposed at an angle to the central longitudinal axis of the stent or stent section containing the cell.

The stent preferably is made of an alloy of nickel and titanium which provides the stent with a thermal memory. The unique characteristic of this alloy, known generally as "Nitinol", is its thermally triggered shape memory, which allows the stent constructed of the alloy to be cooled below a temperature transformation level and thereby softened for loading into a catheter in a relatively compressed and elongated state, and regain the memoried shape when warmed to a selected temperature, above the temperature transformation level, such as human body temperature. The two interchangeable shapes are possible because of the two distinct microcrystalline structures that are interchangeable with a small variation in temperature. The temperature at which the stent assumes its first configuration may be varied within wide limits by changing the composition of the alloy. Thus, while for human use the alloy may be focused on a temperature of 98.6° F. for assumption of the first condition, the alloy readily may be modified for use in animals with different body temperatures.

Although the stents shown in FIGS. 1–4 are preferably formed of wire, they could be formed from a sheet of Nitinol which has been stamped to form the cells 18. Once the cells are formed, the opposed longitudinal edges of the sheet would be joined to form the frame 2 with the straight portions 6 oriented in parallel relationship to the longitudinal axis of the stent.

Figure 5:
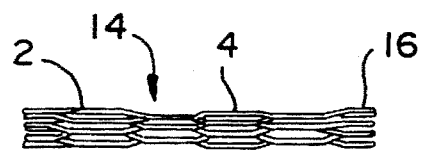
FIG. 5 is a side elevational view of the stent shown in FIG. 1, but shown in a compressed condition.
Figure 7A:
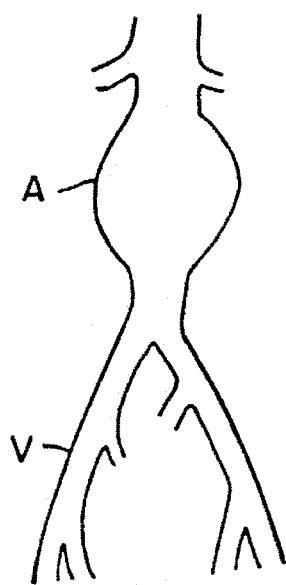
FIGS. 7A–7C are illustrative stylized diagrammatic views of one manner of use of the inventive devices of FIGS. 1–6, as in the treatment of an aneurysm of a large artery.
Figure 7B:
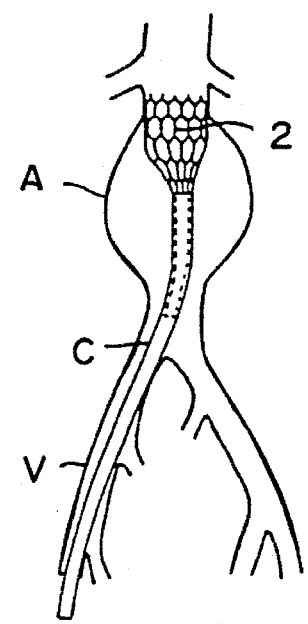

Accordingly, when the stents shown in FIGS. 1–4 are subjected to a temperature at or less than the transition temperature, the relativity rigid stent changes to a second condition in which it is flexible, of reduced stress and collapsible. The stent does not, of its own accord, collapse, or compress, but the stent does become quite pliable, collapsible and compressible. By mechanical means, the stent may be compressed to a point at which the walls 12 of the body portion 14 of the stent frame 2 are positioned against each other, to form a stent diameter substantially equal to the combined thickness of the frame walls in abutting engagement with each other. In FIG. 5, the stent is shown approaching, but not yet having reached such minimal stent diameter. In the compressed condition, the stent is readily contained by a catheter C (FIG. 7B).

Figure 6:
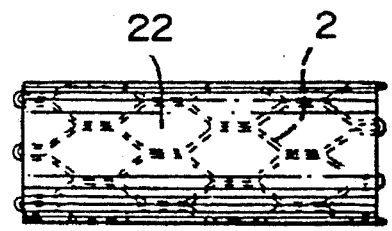
FIG. 6 is a side elevational view of the stent shown in FIGS. 1 and with an elastomeric sleeve thereon.

In FIG. 6, there is shown an alternative embodiment having still further benefits. As noted above, in the second condition of the stent, the stent becomes flexible and compressible, but does not of its own accord compress. In the embodiment shown in FIG. 6, the stent body portion has disposed thereon an elastomeric sleeve 22. The sleeve 22 is expandable on the frame 2 as the frame expands to its enlarged configuration. However, as the sleeve expands, the sleeve exerts a compressive force on the frame. Upon cooling of the stent to or below the transition temperature, the stent becomes flexible and the compressive sleeve 22 urges the frame 2 to a third configuration of smaller diameter than the first configuration. Accordingly, upon cooling of the sleeved embodiment, the flexible frame automatically reduces in size, thereby rendering any repositioning of the stent, as by a grasping tool or other instrument, known in the art (not shown), a relatively simple matter. Again, upon removal of the cooling medium, the sleeved stent returns to its expanded condition.

The sleeved stent has an added benefit in that while an unsleeved stent will suffice in many instances, there are occasions when the affected passageway wall is in such a weakened condition that the provision of a new wall, or a graft, is required. The sleeved stent is essentially a graft and operates to provide a new passageway wall when required.

In operation, the stent, sleeved or unsleeved, is carried through an affected vascular passageway V (FIG. 7A) by the catheter C (FIG. 7B), which is of a thermally insulative material. At room temperature, and while cooled by infusion of a cool solution within the catheter, the stent remains in the second condition, flexible and of low stress. Being of low stress, the stent exercises negligible radial force against the inside wall of the catheter and is easily moved through the catheter at the appropriate time.

Figure 7C:
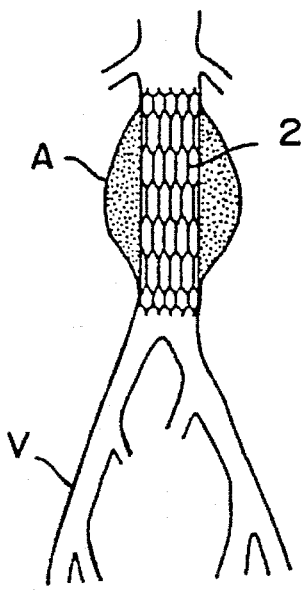

As the catheter enters the passageway V, the thermal insulative properties of the catheter and the flow of cool solution maintain the stent at less than body temperature. When the distal end of the catheter is properly disposed, as for example, in the vicinity of an aneurysm A (FIG. 7B), the stent is moved out of the end of the catheter C. As the stent contacts blood flow, and is subjected to body temperature, the exposed stent immediately and rapidly assumes its first condition, expanding against the walls of the passageway. Upon total ejection of the stent, the catheter is removed, leaving the stent in place to act as an internal wall graft (FIG. 7C).

Figure 8A:
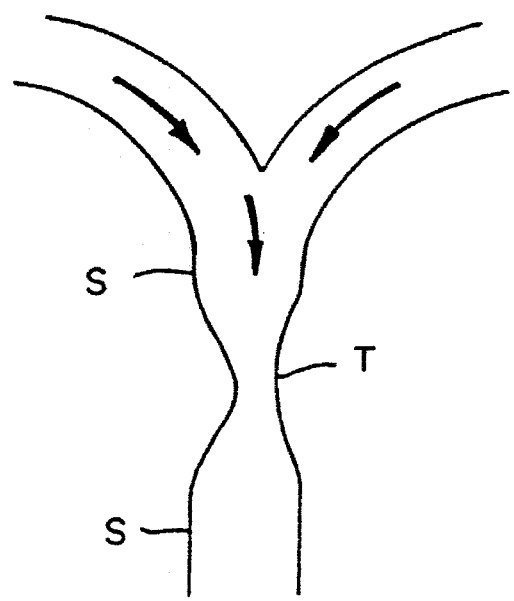
FIGS. 8A–8C are stylized diagrammatic views illustrative of another manner of use of the inventive device of FIGS. 1–6, as in the treatment of compression or narrowing of a vessel.
Figure 8B:
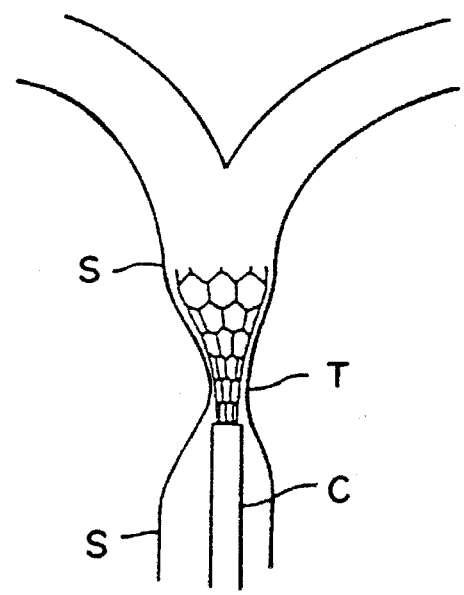
Figure 8C:
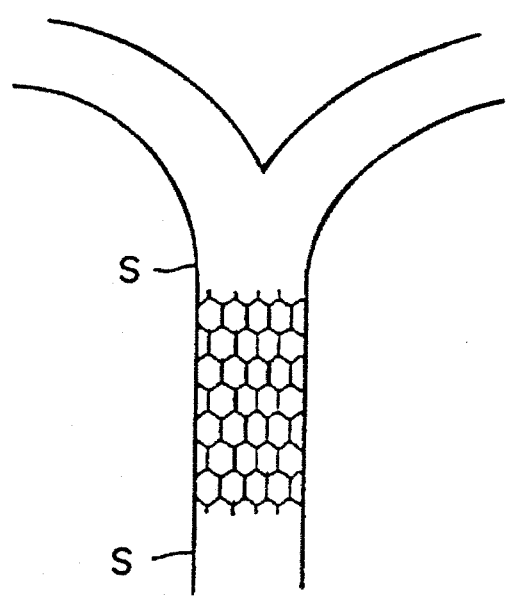

Referring to FIGS. 8A–8C, it will be seen that in treatment of compression of a large vessel, such as a superior vene cava S, the catheter C (FIG. 8B) is moved through the vessel S to a point adjacent a stricture T. The stent 2 is moved from the catheter C, while the catheter is withdrawn, to place the emerging stent within the vessel and in the area of the stricture (FIG. 8B). As the stent emerges from the catheter, the stent, as it is exposed to the blood stream, assumes its first condition. Upon total removal of the stent from the catheter, the stent in its entirety is expanded against the wall of the vessel (FIG. 8C) to maintain the vessel in a free-flowing configuration.

The cell structure and orientation within the stent is very important to the proper expansion and compression characteristics of the stent. Since cell joinder is accomplished solely at adjoining straight portions 6, the expansion of the stent radially and outwardly from the central longitudinal axis or axes thereof places minimal stress on the connections between cells. The straight portions 6, being parallel to the longitudinal axis of the stent or stent section, do not significantly change in configuration as the stent is collapsed and expanded.

Since the sole connection between cells is along these straight portions, the connection is not subjected to tension or shear force during expansion and compression of the stent in a manner which would tend to stress and break the connection. The end walls 21, which are inclined relative to the central longitudinal axis of the stent or stent section, are the portions of the cell which provide the radial memory force during expansion, and the longitudinally oriented connections between the cells causes the cells to distribute this radial memory force evenly around the stent. It is the pliability of the end walls at temperatures below the temperature transformation level which cause the cell straight portions 6 to move together as the stent is compressed, and it is these same end walls which become relatively rigid but resiliently deformable to return the stent to its thermal memory shape at temperatures above the temperature transformation level. As these end walls maintain the straight portions 6 of the cells substantially parallel to the longitudinal axis of the stent in all configurations of the stent, these straight portions are not significantly biased or stressed.

Once expanded in place within a body vessel, a stent is often subjected to forces which tend to crush the stent within the vessel, and known stents, once crushed, are not self expanding. For example, a stent placed in the back of the leg is subjected to forces as the leg bends or is compressed in the seated position of a subject which tend to crush the stent. The stent of the present invention is self expanding if crushed due to the inclined end walls 21. These end walls will flex to permit the straight portions 6 to move inwardly toward the longitudinal axis of the stent or stent section in response to a crushing force, but will spring outwardly to their original memory position once the crushing force is removed.

The ratio of expanded stent diameter to compressed stent diameter can be controlled within limits by selection of wire diameter. The diameter of the expanded stent generally is on the order of 6 to 10 times the diameter of the compressed stent, but can be as great as 20 times that of the compressed stent. In general, the greater the diameter of the wire 4, the less the ratio of the stent collapsed/expanded diameter. By selection of wire diameter, it is possible to vary the radial force which the expanded stent will exert on the interior walls of the passageway in which the stent is set.

Figure 9A:
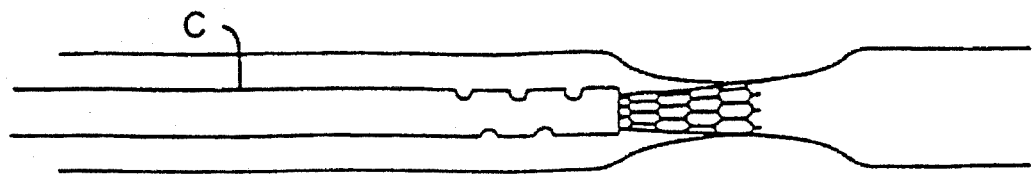
FIGS. 9A–9E are stylized diagrammatic views illustrative of a manner of repositioning the inventive device of FIGS. 1–6.
Figure 9B:
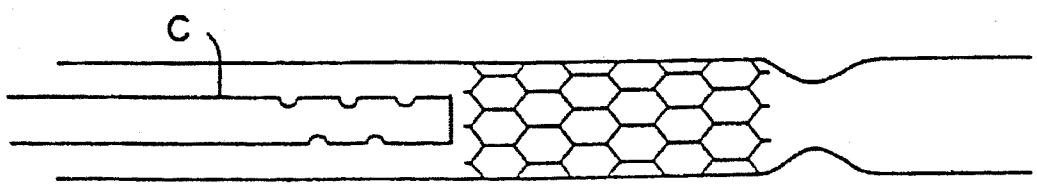
Figure 9C:
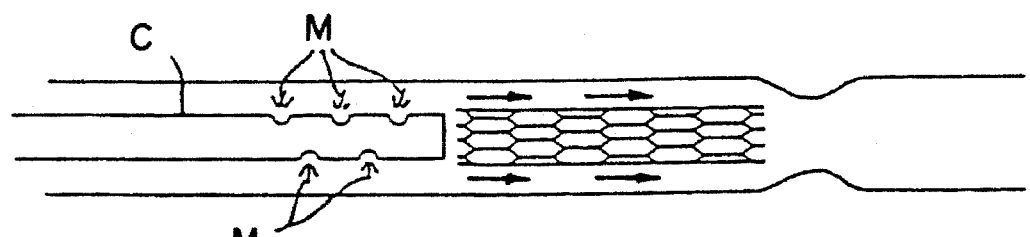
Figure 9D:
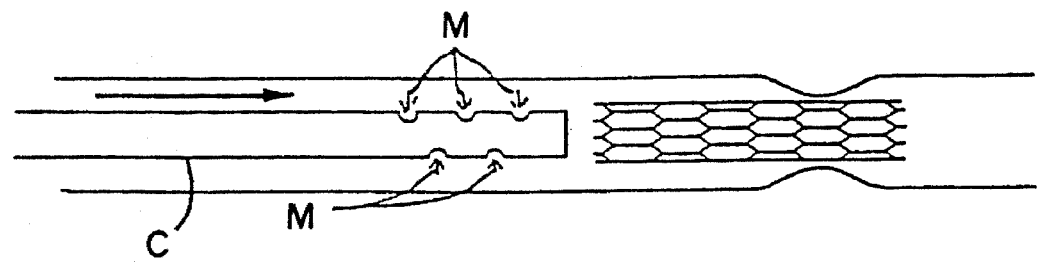
Figure 9E:
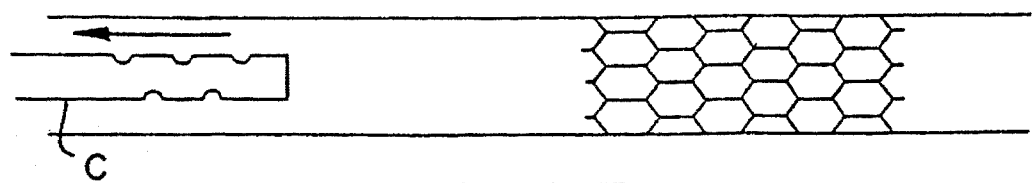

It is sometimes the case that once the stent is in place and in part expanded, it is recognized that the stent is somewhat off target (FIGS. 9A and 9B) and requires repositioning. To reposition the stent of the present invention, the operator introduces into the passageway a cool medium M (FIGS. 9C and 9D), such as a saline solution, having a temperature at or less than the transition temperature. When the cool solution encounters the stent, the stent immediately turns flexible and surrenders radial force against the passageway walls. In such relaxed state, the stent, which has no free wire ends, is easily slid into the proper position by manipulation of the catheter C (FIG. 9D), whereupon the flow of cool solution is stopped and the stent, upon returning to a body temperature, reassumes its expanded condition in the passageway (FIG. 9E). The catheter C is then withdrawn from the stent and from the passageway.

Thus, there is provided a stent which may be alloyed to have a selected temperature at which the stent assumes its first condition and a selected transition temperature, at which the stent assumes its second condition, and which includes a wire frame, wherein the diameter of the wire is selectable to provide a selected degree of expansion force. The stent is compressible to less than a catheter-size diameter to facilitate delivery of the stent to a location within a body passageway by a catheter. The stent may be sleeved or unsleeved. The stent is self-expanding upon delivery from the catheter and introduction to a body temperature, to provide an internal graft or hold open a passageway. Even after such positioning and expansion, the stent is rendered flexible and readily repositionable merely by the flow of a cool medium through the stent. And, finally, by termination of the flow of cool fluid, the stent automatically reassumes its passageway supporting rigid condition. Any required subsequent repositioning can be accomplished in the same manner.

Although the stent of the present invention is generally tubular in configuration since the vessels in which the stent is normally placed are generally tubular, it must be recognized that different portions of these vessels may be sized differently, and therefore the stent must be sized and shaped accordingly. For example, above the renal arteries, the aorta changes size, and therefore a variable sized stent designed to accommodate these changes in shape is required. Referring to FIG. 10, a stent 24 which is formed to fit within a vessel 26 having a variable diameter is illustrated. In its expanded condition, the diameter of the stent increases from a small diameter end 28 to a large diameter end 30. It is desirable to form a stent having a variable outer configuration which will still apply substantially equal outward radial force to the walls of the vessel 26 of varying diameter. As previously indicated, a stent of this type can be formed in several different ways. First, the size of the cells 18 can be varied so that the cell size progressively increases from the small diameter end 28 to the large diameter end 30 as shown in FIG. 10. Thus, the larger cells can be formed to expand the stent to a greater diameter than the smaller cells.

In addition to varying cell size, it is possible to vary the outward radial force of expansion along the length of the stent either in combination with a variation in cell size or with cells of substantially the same size. For example, referring to FIG. 11, a stent 32 is illustrated in expanded condition within a vessel, such as a renal artery 34. The cells 36 at the ends of the stent 32 are defined by Nitinol wire having a thickness or diameter which is much less than that of the cells 38 in the central portion of the stent. Therefore, when expanded, the cells 38, due to the heavier wire, will provide a greater radial force on a artery 34 then will the cells 36 at either end of the stent 32.

It should also be noted that the finger portions at one end of the stent are flared outwardly at 40 when the stent is expanded. This is advantageous for a stent which, for example, is positioned within a renal artery 34, for the flared finger portions 40 will then engage the walls of the aorta 42. When one end of the stent is so flared, the stent will not extend outwardly into the aorta, causing an obstruction, for this is particularly disadvantageous if a second stent, a catheter, or some other device is to be implanted or moved within the aorta. Secondly, tile flared fingers 40 tend to draw back the wall of the aorta as the stent expands opening both the aorta and the renal artery 34. Obviously, the end cells 36 of the stent could be formed to provide the flared portion 40 if no finger portions are included in tile stent design.

Another method for varying the radial outward force applied by the stent would be to anneal sections of the stent at different temperatures so that the temperature transformation level at which various sections of this stent fully expand will vary. For example, the central cells of the stent 32 could be annealed at a temperature which would cause the central section of the stent to fully expand at normal body temperature. The end cells 36 of the stent could be annealed in such a manner that these end cells would fully expand at temperatures slightly higher than normal body temperature, and consequently, at normal body temperature although these end cells would expand, they would not expand to provide full radial force on the vessel 34. Thus, the radial force provided by the end cells 36 would be less than that provided by the center cells 38 at normal body temperature.

The cell expansion characteristics of a stent may be altered by any of the methods described or by the combination of these methods. Thus, cell size could be varied in combination with either a variation in wire size or a variation in annealed temperature, or alternatively, cell size could be maintained constant and a variation in wire size could be combined with the variation in annealed temperature. Ideally, for most stent applications, the central portion of the stent will provide a greater radial force on a vessel than the end portions of the stent, although the end portions should expand sufficiently to anchor the stent in place as a catheter carrying the stent is removed.

Referring now to FIG. 12, the elastomeric, polymeric sleeve 22 illustrated in FIG. 6 may be formed to an extended length so that it can contain a plurality of separate stent sections, two of which are shown at 44 and 46 in FIG. 12. The elongated elastomeric sleeve may be cut apart along cut lines, as indicated at 48, between the stent sections, so that a plurality of stents encased within a sleeve as shown in FIG. 6 may be obtained from the elongated unit of FIG. 12. Alternatively, a single elongated stent could be provided within the sleeve 22, and sections of the stent and sleeve could then be cut to various desired lengths.

In forming the stent of the present invention, it is important to provide a strong bond between cells along the straight portions 6. To accomplish this, the cells of the skeletal frame are first formed of thermal memory wire which has not yet been annealed to achieve its shape memory form and set the expansion shape of the device, and the straight portions 6 are joined by fusion welding, such as by laser welding, to melt together the metal of adjacent straight portions. These welds are initially quite brittle, and consequently, must be subjected to further heat which provides grain growth and forms a ductal weld sufficient to bond the cells firmly together during the expansion of the stent against a vessel wall. Subsequent to the welding process, the stent in the expanded configuration is annealed at a temperature which is sufficient both to set the shape of the stent which will be provided in response to thermal memory and also to render the welds ductal. After this heat treatment, the stent is quenched and is ready for use.

The mechanical behavior of the Nitinol material used to form the stent of the present invention may be enhanced in accordance with the present invention by limiting the twenty three possible martensite variants for the material to a much smaller number and preferentially orienting these variants and/or the grain structure of the alloy in a specific direction dependent on the design requirements of the ultimate device to be formed from the alloy. This orientation can be accomplished with the Nitinol in either its shape memory form or in its superelastic state. To orient the martensitic variants and/or the grain structure of Nitinol, either the wire or the stent being manufactured is subjected to a magnetic field oriented to induce the martensitic variants and/or grain structure to form along a predetermined path which will enhance the mechanical performance of the unit. This process may be carried out at various temperatures depending on the desired effect, and is applicable to binary NiTi alloys but may be even more effective in ternary alloys such as Nitinol with iron (NiTiFe). For the stent of the present invention, the martensitic variants and/or grain structure of the wire is oriented magnetically at an angle to the longitudinal axis of the wire with a preferred angle being ninety degrees. To achieve this orientation, conventional magnetic orientation processes and apparatus can be used, such as those used in Alinco permanent magnet technology.

Referring to FIG. 13, in accordance with the method of the present invention, the thermal memory wire for the stent is wound about pins 50 which project from the surface of a metal heat conducting mandrel 52. It will be noted that for each cell 18, four pins 50 are provided, with a pin being positioned at each end of a straight portion 6 for the cell where the straight portion meets the cell end wall 21. Thus, the pins define the extent of the straight portions for each cell. When the stent includes finger portions 16, additional pins are positioned around the mandrel 52 at the ends of the stent to form these finger portions.

In the formation of the mandrel 52, the mandrel is placed in a jig and the holes for the pins 50 are drilled in the mandrel in accordance with a position program in the central processing unit 54 of a computer controlled drilling unit 56. The pins are then inserted in the mandrel, and once they receive the wire 4, the program in the central processing unit controls a laser welder 58. Since the pins determine the extent of the straight portions 6 to be welded, the laser welder 58 may be controlled by the program in the central processing unit which programs the location of the pins so that the welder creates a weld between the pins at the ends of the straight portions 6. It is possible to configure the jig to allow for the laser beam to be focused through the jig on one side to the weld zone on the inside (luminal side) of the device. Thus fusion welds can be created on both the outer surface and the inner surface of the device. Once all of the welds are formed, the mandrel is placed in an annealing oven which heats both the mandrel 52, the welds, and the wire 4 to set the expanded memory configuration of the stent. Then the mandrel is removed and quenched, and this cooling of the mandrel and the wire 4 causes the stent to become flexible and expand sufficiently to be removed over the pins 50 of the mandrel 52.

Most stents are delivered following the insertion of a guide wire and catheter into the obstructed structure, such as an artery or other vessel. The catheter serves to guide the insertion of the stent and protect the stent from being displaced as it is being pushed. Once the stent is properly positioned, the catheter is usually pulled back over the top of the stent so that the stent can then be expanded. Normally, the distal end of the device is exposed first during the delivery procedure.

There are instances, however, where the preferred delivery of stent devices is proximal end first. This is especially true when attempting to accurately place steals in the ostium or mouth of a tubular structure, e.g. the renal artery at the aorta as shown in FIG. 11. If the proximal end of the stent is flared outward and the proximal end of the stent can be delivered first, then it is possible to place the stent in perfect apposition to the ostium where the proximal end of the device is anchored and the distal portion of the stent is delivered last. This eliminates the usual need to leave some portion of the stent device protruding into the lumen of the aorta.

Referring to FIG. 14, a novel two piece stent delivery unit indicated generally at 60 is shown for placing a stent within a vessel so that the proximal end of the stent is the first end to be expanded and anchored. This delivery unit includes a dilator section 62 and a sheath section 64 which is an open ended, elongate tube that slides onto the dilator section. The dilator section includes a central tubular body having an enlarged portion 66 with an outer diameter that is sized to be slightly smaller than the inner diameter of the sheath section 64 so that the sheath section will slide relative to the central tubular body. This central tubular body also includes a portion of reduced diameter 68 which extends outwardly from the enlarged portion to a tapered dilator tip 70. Extending rearwardly frown the dilator tip, spaced from and concentric with the portion 68, is an outer tube 72 which terminates in spaced relationship to the enlarged portion 66. The outer tube has an outer diameter which is substantially equal to the outer diameter of the enlarged portion 66 and is adapted to slidably receive the sheath section 64. The outer tube defines an annular space 74 between the outer tube and the portion 68 of the central tubular body. A central longitudinal passage 76 which is open at both ends extends completely through the dilator section 62.

In the operation of the stent delivery unit 60 as shown by FIGS. 15A–15E, a stent, such the flanged stent 32 of FIG. 11 (shown in broken lines) is inserted into the space 74 between the outer tube 72 and the reduced portion 68 with the distal end of the stent positioned adjacent to the dilator tip 70. The proximal end of the stent with the flanged portion 40 is positioned outside the space 74 between the outer tube 72 and the enlarged portion 66 of the central tubular body. The sheath section 64 is then moved into place over the enlarged portion 66 and the outer tube 72 to enclose the proximal end of the stent as shown in FIG. 15A. With the stent so enclosed, a guidance wire 78 may be inserted through the central longitudinal passage 76 to aid in guiding the stent delivery unit into place in a vessel, such as the renal artery 34.

With the stent 32 properly located, the sheath section 64 is drawn back away from the outer tube 72 as shown in FIG. 15B to expose the proximal end of the stent. This proximal end, when subjected to normal body temperature, now expands into contact with the vessel to anchor the stent in place. When a flared stent 32 is used for the treatment of ostial type lesions, the stent would be located at the ostium and held in place by contact between the flared portion 40 and a parent structure, such as the wall of the aorta 42.

Once the proximal end of the stent is anchored in place, the dilator section 62 is moved within the sheath section 64 into the vessel 34, as shown in FIGS. 15C and 15D, until the entire stent is exposed and the distal end is released from the space 74. The entire stent is now subjected to body temperature and is designed to expand against the vessel 34 to reach an inner diameter which is greater than the outer diameter of the stent delivery unit 60. Now, with the stent 32 expanded within the vessel 34, the stent delivery unit is withdrawn through the expanded stent as shown in FIG. 15E.

It is to be understood that the present invention is by no means limited to the particular constructions herein disclosed and/or shown in the drawings, but also comprises any modifications or equivalents within the scope of the claims. For example, while the use of the stent has been illustrated in connection with the vascular system, it will be apparent to those skilled in the art that the stent herein shown and described finds equal utility in other bodily passageways.

We claim:

1. A stent comprising an elongate body member having a longitudinal axis with a skeletal frame formed to define an elongate chamber which extends through said body member, the body member being formed of thermal shape memory material which operates in response to temperature to expand or contract said skeletal frame between a first expanded configuration and a second compressed configuration, said body member including a plurality of interconnected, open cells forming the skeletal frame of said body member, each of said cells including two substantially parallel, spaced side portions which are substantially parallel to said longitudinal axis and end wall means extending between said side portions at an angle to said longitudinal axis, said end wall means operating to maintain said cell straight side portions substantially parallel to said longitudinal axis in both said first expanded configuration of said skeletal frame and in said second collapsed configuration.

2. The stent of claim 1 wherein said cells are formed of at least one elongate strand of shape memory material and joined together only along the lengths of said straight portions.

3. The stent of claim 1 wherein said shape memory material has a temperature transformation level above which said skeletal frame assumes a first expanded configuration relative to said longitudinal axis and below which said cell end wall means permit movement of said straight portions toward said longitudinal axis to collapse said skeletal frame to a second collapsed configuration, said cells being interconnected only at said straight side portions with no connection between the end wall means thereof.

4. The stent of claim 3 wherein said cell end wall means operate at a temperature above said temperature transformation level when said skeletal frame is in the second collapsed configuration to expand the skeletal frame to the first expanded configuration.

5. The stent of claim 4 wherein said end wall means operate to cause the space between the straight side portions of said cells to decrease in order to collapse said skeletal frame to the second collapsed configuration.

6. The stent of claim 5 wherein said cell end wall means are relatively pliable when said skeletal frame is subjected to temperatures below said temperature transformation level and are resiliently deformable but relatively rigid when said skeletal frame is subjected to temperatures above said temperature transformation level.

7. The stent of claim 5 wherein said cells are polygonal in shape.

8. The stent of claim 7 wherein said cells are hexagonal in shape.

9. The stent of claim 5 wherein said cells are joined together only along the lengths of said straight portions.

10. The stent of claim 5 wherein said cell end wall means each include first and second wall sections, each said wall section having a first end joined to one of the side portions of said cell, said wall section extending at an angle to the side portion to which the first end thereof is joined, and each said wall section having a second end opposite to said first end, the second ends of said first and second wall sections being joined.

11. The stent of claim 5 wherein said skeletal frame includes cells of different sizes.

12. The stent of claim 5 wherein the side portions and end wall means of some cells in said skeletal frame are formed to have a greater cross-sectional area than the side portions and end wall means of other cells in said skeletal frame.

13. The stent of claim 5 wherein the thermal shape memory material forming the side portions and end wall means of some cells in said skeletal frame has a temperature transformation level which differs from the temperature transformation level of the thermal shape memory material forming the side portions and end wall means of other cells in said skeletal frame.

14. The stent of claim 4 wherein said body member includes opposed open ends, said elongate chamber extending between said open ends, the skeletal frame adjacent to at least one of said open ends being formed to provide laterally extending means annularly of said open end in said first expanded configuration.

15. A stent for insertion in a body vessel comprising an elongate body means having a longitudinal axis, a first end, a second end, and an elongate chamber extending through said body means between said first and second ends, the body means being formed of thermal shape memory material which is relatively pliable at temperatures below a transition temperature to permit said body means to be collapsed toward said longitudinal axis to a collapsed configuration, for insertion in said body vessel, said thermal shape memory material operating to expand said body means radially outward from said collapsed configuration toward an expanded memory configuration in response to said transition temperature to contact and apply force to said body vessel, said body means operating at said transition temperature to apply less force to said body vessel in the area of at least one of said first and second ends than the force applied by the remainder of said body means to said body vessel at the transition temperature.

16. A method for forming a stent of thermal shape memory material which becomes pliable to permit the stent to be collapsed at temperatures below a temperature transformation level and which expands the collapsed stent to a preset memory shape at temperatures above the temperature transformation level which includes the steps of forming a plurality of open cells from thermal shape memory material, fusion welding the thermal shape memory material to form a stent body member with an elongate chamber extending therethrough, and subsequently annealing said body member at a temperature sufficient to set the memory shape of said stent while rendering ductile the fusion welds.

17. The method of claim 16 which includes placing at least one elongate strand of thermal shape memory material on a heat conductive mandrel to form said plurality of open cells, joining said open cells on said heat conductive mandrel by fusion welding to form said stent body member, and subsequently annealing said stent body member on said heat conductive mandrel.

18. The method of claim 17 which includes forming a plurality of adjacent open cells which extend completely around said mandrel, each such cell being formed with two spaced, substantially parallel side walls arranged to extend substantially parallel to the longitudinal axis of said mandrel and joining said cells by fusion welding only along the sidewalls of adjacent cells.

19. A stent comprising an elongate body member having a longitudinal axis with a skeletal frame formed to define an elongate chamber which extends through said body member, the skeletal frame being formed to assume a first expanded configuration relative to said longitudinal axis and to be collapsible toward said longitudinal axis to a second collapsed configuration, said skeletal frame further being formed to define a plurality of interconnected open cells with each of said cells including two substantially parallel, spaced side walls which are substantially parallel to said longitudinal axis in both the first expanded configuration and the second collapsed configuration of said skeletal frame and end walls extending between said sidewalls at an angle to said longitudinal axis, said cells being arranged around said elongate chamber with sidewalls of adjacent cells arranged in adjacent coextensive relationship, said cells joined together by an attachment connecting adjacent, coextensive cell sidewalls, this being the only connection between said cells.

20. The stent of claim 19 wherein said cells are polygonal in shape.

21. The stent of claim 20 wherein said cells are hexagonal in shape.

22. The stent of claim 19 wherein said cell end walls each include first and second wall sections, each said wall section having a first end joined to one of the sidewalls of said cell, said wall section extending at an angle to the sidewall to which the first end thereof is joined, and each said wall section having a second end opposite to said first end, the second ends of said first and second wall sections being joined.

23. A stent comprising an elongate body member having a first section, a second section, a longitudinal axis and an elongate chamber which extends through said body member, the body member being formed of thermal shape memory material having a temperature transformation level above which said body member assumes an expanded configuration relative to said longitudinal axis and below which said body member may be collapsed to a collapsed configuration, the shape memory material in said first section of said body member having a temperature transformation level which differs from the temperature transformation level of the shape memory material in said second section of said body member.

24. A stent comprising an elongate body member having a longitudinal axis with a skeletal frame formed to define an elongate chamber which extends through said body member, the body member being formed of thermal shape memory material which has been annealed at a temperature sufficient to set a memory shape for said body member and impart to said shape memory material a temperature transformation level above which said skeletal frame assumes a first expanded configuration relative to said longitudinal axis and below which said skeletal frame will be collapsible toward said longitudinal axis to a second collapsed configuration, said thermal shape memory material being formed to define a plurality of interconnected open cells forming the skeletal frame of said body member with each of said cells including two substantially parallel, spaced side portions which are substantially parallel to said longitudinal axis in both the first expanded configuration and the second collapsed configuration of said skeletal frame and end wall means extending between said side portions at an angle to said longitudinal axis, said cells being joined together only along said side portions by fusion welds formed prior to the annealing of said shape memory material.

25. The stent of claim 24 wherein the thermal shape memory material forming the side portions and end wall means of some cells in said skeletal frame has a temperature transformation level which differs from the temperature transformation level of the thermal shape memory material forming the side portions and end wall means of other cells in said skeletal frame.

26. The stent of claim 24 wherein said cell end wall means each include first and second wall sections, each said wall section having a first end joined to one of the side portions of said cell, said wall section extending at an angle to the side portion to which the first end thereof is joined, and each said wall section having a second end opposite to said first end, the second ends of said first and second wall sections being joined, said end wall means being relatively pliable when said skeletal frame is subjected to temperatures below said temperature transformation level and resiliently deformable but relatively rigid when said skeletal frame is subjected to temperatures above said temperature transformation level and operating while maintaining said cell straight side portions substantially parallel to said longitudinal axis to cause the space between the straight side portions of said cells to decrease in order to collapse said skeletal frame from the first expanded configuration to the second collapsed configuration and to cause the space between the straight side portions of said cells to increase to expand said skeletal frame from the second collapsed configuration to the first expanded configuration.

27. A stent comprising an elongate body member having a longitudinal axis and a skeletal frame formed to define an elongate chamber which extends through said body member, the body member being formed of thermal shape memory material which defines a plurality of interconnected, open cells forming the skeletal frame of said body member, each of said cells including two substantially parallel, spaced, straight side portions which are substantially parallel to said longitudinal axis and end wall means extending between said side portions at an angle to said longitudinal axis, said cells being joined together only along the lengths of said straight side portions, the shape memory material having a temperature transformation level above which said skeletal frame assumes a first expanded configuration relative to said longitudinal axis and below which said cell end wall means permit the space between straight side portions of said cell to decrease to permit movement of said straight portions toward said longitudinal axis to collapse said skeletal frame to a second collapsed configuration, said cell end wall means operating at a temperature above said temperature transformation level when said skeletal frame is in the second collapsed configuration to expand the skeletal frame to the first expanded configuration, and elastomeric sleeve means disposed around said elongate body and operating to expand when said skeletal frame assumes said first expanded configuration and to exert a compressive force on said skeletal frame in said first expanded configuration, said elastomeric sleeve means operating when said skeletal frame is at or below said transition temperature to collapse said skeletal frame to the second collapsed configuration.

28. The stent according to claim 27 wherein a first area of said skeletal frame includes cells which are larger than the cells in at least a second area of said skeletal frame, said cells in said first and second areas expanding at temperatures above said transition temperature to apply a radial force against said elastomeric sleeve means with the radial force applied by the cells in said first area being different from the radial force applied by the cells in said second area.

29. The stent of claim 27 wherein said skeletal frame, when expanded, is substantially tubular in configuration with rows of six interconnected cells defining the circumference of the frame and an even number of cells along the length of the frame.

30. A stent for insertion in a body vessel comprising an elongate body means having a longitudinal axis, a first end, a second end, and an elongate chamber extending through said body means between said first and second ends, the body means being formed of thermal shape memory material which is relatively pliable at temperatures below a transition temperature to permit said body means to be collapsed toward said longitudinal axis to a collapsed configuration for insertion in said body vessel, said thermal shape memory material operating to expand said body means radially outward from said collapsed configuration toward an expanded memory configuration in response to temperatures at or above said transition temperature to contact and apply radial force to said body vessel, said body means including a skeletal frame formed of said thermal shape memory material to define said elongate chamber, the skeletal frame including a plurality of interconnected open cells, each of which includes two substantially parallel, spaced, straight side portions which are substantially parallel to said longitudinal axis and end wall means extending between said side portions at an angle to said longitudinal axis, said cells being joined together only along the lengths of said straight side portions, said skeletal frame including a first area including cells which are designed differently from cells in at least a second area of said skeletal frame to cause different radial forces to be applied to said body vessel by said body means in the expanded memory configuration thereof.

31. The stent according to claim 30 wherein the cells in said first area of the skeletal frame are formed at a greater angle to the longitudinal axis of said body means than are the endwalls of the cells in the second area of said frame.

32. The stent according to claim 30 wherein each cell in said first area of said skeletal frame includes two substantially parallel spaced straight side portions which are spaced apart for a distance substantially equal to the distance between the substantially parallel spaced side portions of the cells in said second area of said skeletal frame, the endwall means of the cells in said first area being greater in length than the endwall means of the cells in said second area to form cells of greater length in the longitudinal direction of said body means.

* * * * *